United States Patent
König

(10) Patent No.: US 11,898,979 B2
(45) Date of Patent: Feb. 13, 2024

(54) GAS SENSOR WITH IMPROVED SENSITIVITY AND GAS SENSOR COMPONENT

(71) Applicant: TDK Corporation, Tokyo (JP)

(72) Inventor: Matthias König, Munich (DE)

(73) Assignee: TDK Corporation, Tokyo (JP)

( * ) Notice: Subject to any disclaimer, the term of this patent is extended or adjusted under 35 U.S.C. 154(b) by 339 days.

(21) Appl. No.: 17/031,242

(22) Filed: Sep. 24, 2020

(65) Prior Publication Data

US 2021/0096095 A1 Apr. 1, 2021

(30) Foreign Application Priority Data

Sep. 26, 2019 (DE) .......................... 102019126025.6

(51) Int. Cl.
*G01N 27/16* (2006.01)
*G01N 33/00* (2006.01)
*G01N 27/12* (2006.01)

(52) U.S. Cl.
CPC ........... *G01N 27/16* (2013.01); *G01N 27/123* (2013.01); *G01N 33/0027* (2013.01)

(58) Field of Classification Search
CPC .... G01N 27/16; G01N 27/18; G01N 33/0031; G01N 33/004; G01N 27/028; G01N 27/122; G01N 27/123; G01N 27/124; G01N 27/125; G01N 27/185; G01N 27/3271; G01N 33/006; G01N 33/497; G01F 1/6847; G01F 1/6965; G01F 1/698; G01F 1/699; G01K 7/20; G01R 17/105; G01R 17/18; H04B 1/109; Y10T 29/49; Y10T 29/49002; Y10T 436/11
See application file for complete search history.

(56) References Cited

U.S. PATENT DOCUMENTS

| 6,125,695 A * | 10/2000 | Alvesteffer | G01F 1/698 |
| | | | 73/204.27 |
| 6,606,488 B1 * | 8/2003 | Konig | H04B 1/109 |
| | | | 455/295 |
| 2004/0065140 A1 * | 4/2004 | Bristol | G01N 27/16 |
| | | | 73/25.05 |

(Continued)

FOREIGN PATENT DOCUMENTS

| CA | 2660896 C * | 5/2012 | ........... G01F 1/6965 |
| DE | 4025875 A1 | 2/1992 | |

(Continued)

OTHER PUBLICATIONS

Herz-Online-Hochschule Karlsruhe Technik und Wirstchaft, "Schmitt-Trigger-Schaltungen," Web page, <URL: https://www.eit/hs-karlsruhe.de/hertz/teil-b-gleichstromstechnik/operationsverstä rker/schmitt-trigger-schaltungen/invertierende-schmitt-trigger-schaltung.html>, Retrieved from the Internet on Oct. 6, 2020 (2 pages).

*Primary Examiner* — Harshad R Patel
*Assistant Examiner* — Gedeon M Kidanu
(74) *Attorney, Agent, or Firm* — Nixon Peabody LLP

(57) ABSTRACT

A gas sensor with improved sensitivity. The gas sensor comprises an active sensor unit, a reference sensor unit and a temperature control circuit. The active sensor unit has an active detector. The reference sensor unit has a reference detector. The temperature control circuit is provided and configured to keep a detector at a predetermined temperature.

11 Claims, 2 Drawing Sheets

(56) References Cited

U.S. PATENT DOCUMENTS

| | | | | |
|---|---|---|---|---|
| 2008/0101434 A1* | 5/2008 | Horovitz | .............. | G01N 27/123 |
| | | | | 374/45 |
| 2008/0226505 A1* | 9/2008 | Willettt | ................. | G01N 27/16 |
| | | | | 73/23.21 |
| 2016/0011134 A1 | 1/2016 | Kuemin | | |

FOREIGN PATENT DOCUMENTS

| | | | | | |
|---|---|---|---|---|---|
| DE | 4025875 | A1 | * | 2/1992 | |
| DE | 4221922 | C1 | | 1/1994 | |
| EP | 2762867 | A1 | | 11/2018 | |
| JP | 2016050825 | A | * | 4/2016 | |
| JP | 2017156293 | A | * | 9/2017 | |
| JP | 2017166826 | A | * | 9/2017 | |
| JP | 2018036174 | A | * | 3/2018 | |
| JP | 2018205105 | A | * | 12/2018 | |
| JP | 2019060848 | A | * | 4/2019 | ........... G01N 27/122 |
| JP | WO2020129341 | A1 | * | 10/2021 | |
| WO | WO-2018135100 | A1 | * | 7/2018 | ........... G01N 27/028 |
| WO | WO-2019065127 | A1 | * | 4/2019 | ........... G01N 27/122 |
| WO | WO-2020129341 | A1 | * | 6/2020 | ............. G01N 27/18 |

* cited by examiner

GAS SENSOR WITH IMPROVED SENSITIVITY AND GAS SENSOR COMPONENT

The present invention refers to gas sensors with an improved sensitivity and to corresponding components.

Gas sensors can be used to detect the presence of a specific gas or to provide a concentration of a specific gas in an atmosphere.

One example of a gas sensor is a catalytic pellistor. The catalytic pellistor works by burning the to-be-detected or quantified gas. The generated heat causes a change in the resistance of a detecting element. By measuring the change or the resistance, the concentration of the corresponding gas can be determined.

From EP 2762867 A1, US 2008/0101434 A, US 2004/0065140 A1 and DE 112006000973 B4 gas sensors are known.

However, known gas sensors do not provide a reliable signal when the ambient temperature or the ambient humidity is changing. Further, known gas sensors suffer from reliability problems due to gas and used high temperatures, signal stability problems due to asymmetries in sensors, and a non-homogeneous distribution of catalytic material.

Thus, what is needed is a gas sensor that provides an improved sensitivity even at varying ambient temperatures and humidity levels, that has reduced power consumption, that has a simplified construction and that provides an output signal that is easy to handle.

To that end, a gas sensor according to independent claim 1 is provided. Dependent claims provide preferred embodiments.

The gas sensor comprises an active sensor unit and a reference sensor unit. The active sensor unit has an active detector and a heater. The reference sensor unit has a reference detector and a heater. Further, the gas sensor comprises a temperature control circuit. The temperature control circuit is provided and configured to keep a detector that can be selected from the active detector and the reference detector at a predetermined temperature.

The presented gas sensor follows the counter-intuitive approach because it comprises a detector that is kept at a predetermined, constant temperature by the temperature control circuit while conventional gas sensors detect gases based on a corresponding temperature change.

However, the provided gas sensor allows monitoring a temperature difference, specifically a temperature difference between the temperature of the active detector and of the reference detector when one of these two detectors is kept at the predetermined temperature. Specifically, the sensitivity of the gas sensor is improved because one of the two detectors is kept at the constant predetermined temperature, which makes the gas sensor's output independent from a change in the ambient temperature or ambient humidity.

It is possible that the gas sensor comprises a catalyst.

Specifically, it is possible that the active sensor unit comprises a catalyst.

The catalyst makes the corresponding sensor unit being the active sensor unit because the catalyst—when kept at a predetermined temperature by thermal coupling to the corresponding heater—provides a predetermined gas conversion rate depending on the concentration of the to-be-detected gas but not on the ambient temperature or humidity.

It is possible that the catalyst determines the gas selectivity.

To that end, the catalyst can be chosen according to its conversion rate for one or more specific gases. For example, the catalyst for a carbon monoxide detector can be chosen to accelerate the conversion of oxygen and carbon monoxide to carbon dioxide. The dissipating heat being the base for determining an output signal based on a reduced or increased power requirement to maintain the corresponding detector at the predetermined temperature.

Further, it is possible that the catalyst has a large surface area and is in direct contact with a detecting element of the active detector.

Catalysts for the gases carbon monoxide (CO), hydrogen (H, H2) and methane (CH4) can be selected from platinum (Pt), palladium (Pd) and rhodium (Rh), respectively.

It is possible that the active detector and the reference detector are electrically connected in series.

Specifically, it is possible that the active detector and the reference detector are electrically connected in series between a ground potential and a supply potential $V_{cc}$. A second node can be arranged between the active detector and the reference detector. A potential difference between the supply potential and the potential at the node between the two detectors or a potential difference (voltage) between the potential at the second node and the ground potential can be a primary output signal of the gas sensor.

The active detector can comprise a resistance element covered with the catalyst being in direct contact with the to-be-evaluated atmosphere.

The reference detector can comprise a resistance element electrically connected between the second node and the ground potential.

Further, the heater of the active sensor unit can comprise a resistance element. Further, the heater of the reference detector can comprise a resistance element.

It is possible that the heater of the active sensor and the heater of the reference sensor are electrically connected in parallel.

Specifically, it is possible that the two heaters are electrically connected in parallel with respect to a temperature control circuit and a ground potential. Thus, the heater of the active sensor unit can be electrically connected between a temperature control circuit and a ground potential and the heater of the reference sensor unit can be electrically connected between the temperature control circuit and the ground potential in parallel to the heater of the active sensor unit.

Correspondingly, it is possible that the temperature control circuit provides—when the gas sensor is active—electrical power to the heaters of the active sensor unit and the reference sensor unit.

Further, it is possible that the temperature control circuit provides the same amount of electrical power to each of the two heaters or that the temperature control circuit maintains the predetermined electrical power ratio with respect to the electrical powers provided to the two heaters.

It is possible that the active detector is thermally coupled to the heater of the active sensor unit. Further, it is possible that the reference detector is thermally coupled to the heater of the reference sensor unit.

Specifically, it is possible and preferred that the temperature control circuit is provided and configured to keep the active detector at the predetermined temperature.

Further, it is possible that the active detector and/or the reference detector has/have a temperature-dependent resistance.

Thus, the heater of the active sensor unit keeps the active detector at a predetermined temperature. When a specific amount of to-be-detected gas is converted, the temperature control circuit correspondingly reduces the amount of provided power. To that end, the temperature control circuit can have a feedback loop including the active detector.

Since the two heaters can obtain the same amount of electrical power, when the heater of the active sensor unit requires less power, the temperature of the reference detector drops and the overall circuit of the gas sensor is operated at the reduced electric power, saving electric energy and preventing temperature-induced instabilities and increasing the reliability of the gas sensor.

It is possible that the temperature control circuit comprises an operational amplifier. The operational amplifier can have an inverted input, a non-inverted input and an output.

Further, it is possible that the operational amplifier is electrically coupled to the heater of the active sensor unit and to the heater of the reference sensor unit.

Specifically, it is possible that the inverted input is coupled to a supply potential. The non-inverted input can be coupled to a first node. The first node is arranged at the output side of the heater of the active sensor unit. The output side of the heater of the active sensor unit is the connection of the heater pointing towards a ground potential while the corresponding other, input side points toward the temperature control circuit.

It is possible that the gas sensor comprises a series connection of a first resistance element and of a second resistance element, having a node between the two resistance elements. The first resistance element can be provided and configured to be connected to the supply potential while the respective other, second resistance element can be provided and configured to be connected to the ground potential.

It is possible that the inverted input of the operational amplifier is electrically connected to the node between the first and the second resistance elements. This node acts as the power supply for the temperature control circuit.

It is possible that the gas sensor comprises a signal port. The signal port can have a connection coupled to a second node. The second node can be arranged between the active detector and the reference detector.

The provided electrical potential at the signal port, e.g. with respect to a ground potential or with respect to the supply potential encodes a signal depending on the concentration of the to-be-evaluated gas of the atmosphere of the gas sensor.

Further, it is possible that the gas sensor additionally comprises an evaluation circuit. The evaluation circuit can be connected to the signal port.

It is possible that the evaluation circuit comprises an application-specific integrated circuit (ASIC), a microcontroller (MCU) and/or an analog-to-digital converter.

Specifically, it is preferred that the evaluation circuit comprises an analog-to-digital converter for being able to provide a digital output signal to a circuit environment of the gas sensor.

The signal provided by the evaluation circuit can be directly proportional to the concentration of the to-be-monitored gas in the atmosphere surrounding the gas sensor.

A gas sensor component can comprise a gas sensor as described above. The active sensor unit can be arranged at a membrane at the top side of a base material of the gas sensor component. The base material can be arranged on or above a carrier substrate. The carrier substrate can comprise a recess.

It is preferred that the membrane is thin. Then the thermal inertia is reduced and response times to a variation of the to-be-detected gas are reduced. Further, energy dissipation is reduced. Thus, energy drain and power consumption are also reduced.

Such a gas sensor can have a power consumption in the mW range, e.g. between 1 and 40 mW, and provide a sensitivity in the ppm (parts per million) range, e.g. between 1 ppm and 10 ppm or between 10 ppm and 100 ppm or between 100 ppm and 1000 ppm or between 1000 ppm and 10000 ppm or between 1 ppm and 10000 ppm.

Working principles and details of preferred embodiments are shown in the accompanying schematic Figures.

Figure 1:
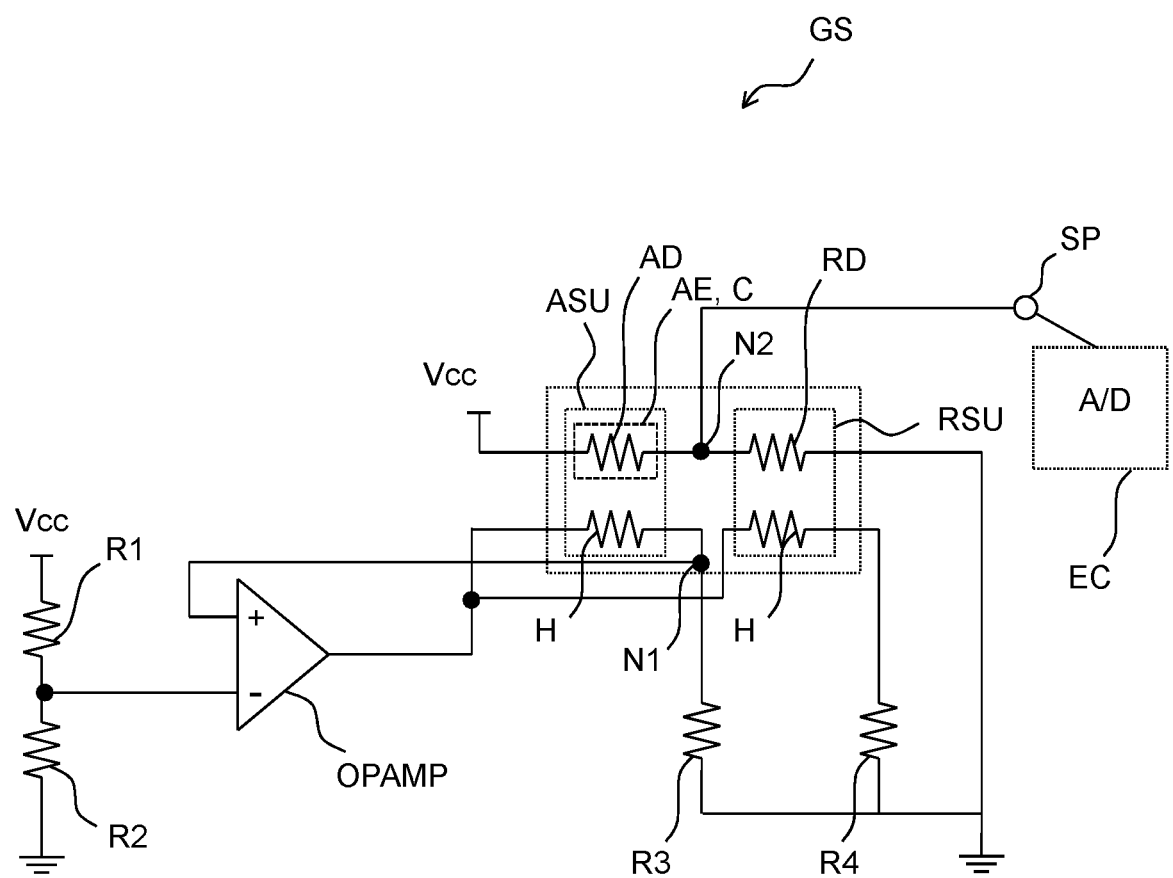
FIG. 1 shows circuit elements of an equivalent circuit diagram of the gas sensor.

FIG. 1 shows circuit elements of an equivalent circuit diagram of the gas sensor GS. The gas sensor GS has an active sensor unit ASU and a reference sensor unit RSU. Further, the gas sensor has a temperature control circuit comprising an operational amplifier OPAMP. Further, the gas sensor has a first resistance element R1 and a second resistance element R2 and a third resistance element R3 and a fourth resistance element R4. Further, the gas sensor has an analog-to-digital converter A/D.

The active sensor unit ASU comprises an active detector AD and a heater H. The reference sensor unit RSU comprises a reference detector RD and a heater H. The active detector AD comprises an active element AE, e.g. a catalyst covering at least partially the material of the active detector and being in direct contact with the to-be-monitored atmosphere.

The active detector AD and the reference detector RD are electrically connected in series between a supply potential $V_{cc}$ and a ground potential. Specifically, the active detector AD is electrically connected between the reference potential $V_{cc}$ and the second node N2. The reference detector is electrically connected between the second node N2 and the ground potential. Further, the second node N2 is electrically arranged between the active detector AD and the reference detector RD.

The second node N2 is connected to the signal port SP, where an analog output signal of the gas sensor GS is provided. An evaluation circuit EC, e.g. comprising an analog-to-digital converter A/D, can be comprised in the evaluation circuit EC to provide a digital output signal to an external circuit environment.

The heater H of the active sensor unit is formally coupled to the active detector AD and electrically connected between the output of the operational amplifier OPAMP and the ground potential. The heater H of the reference detector RD is also electrically connected between the output of the operational amplifier OPAMP and the ground potential. With respect to the operational amplifier and the ground potential the two heaters are electrically connected in parallel. A feedback signal line electrically connects the output side at the first node N1 of the heater H of the active sensor unit ASU to the non-inverted input of the operational amplifier.

The inverted input of the operational amplifier is electrically connected to a node between the first resistance element R1 and the second resistance element R2, establishing a series connection between the supply potential $V_{cc}$ and ground. Thus, because the heater H of the active sensor unit ASU can have a temperature-dependent resistance, the heater H of the active sensor unit can be kept at a constant and predetermined temperature. Via the thermal coupling between the heater H of the active sensor unit and the active detector, the active detector can be kept at the constant, predetermined temperature, improving the reliability of the output signal of the gas sensor.

A third resistance element R3 is electrically connected between the first node N1 and the ground potential. A fourth resistance element R4 can be electrically connected between the heater H of the reference sensor unit RSU and the ground potential. The third and the fourth resistance element can be used to determine the ratio of electrical powers provided to the two heaters.

Figure 2:
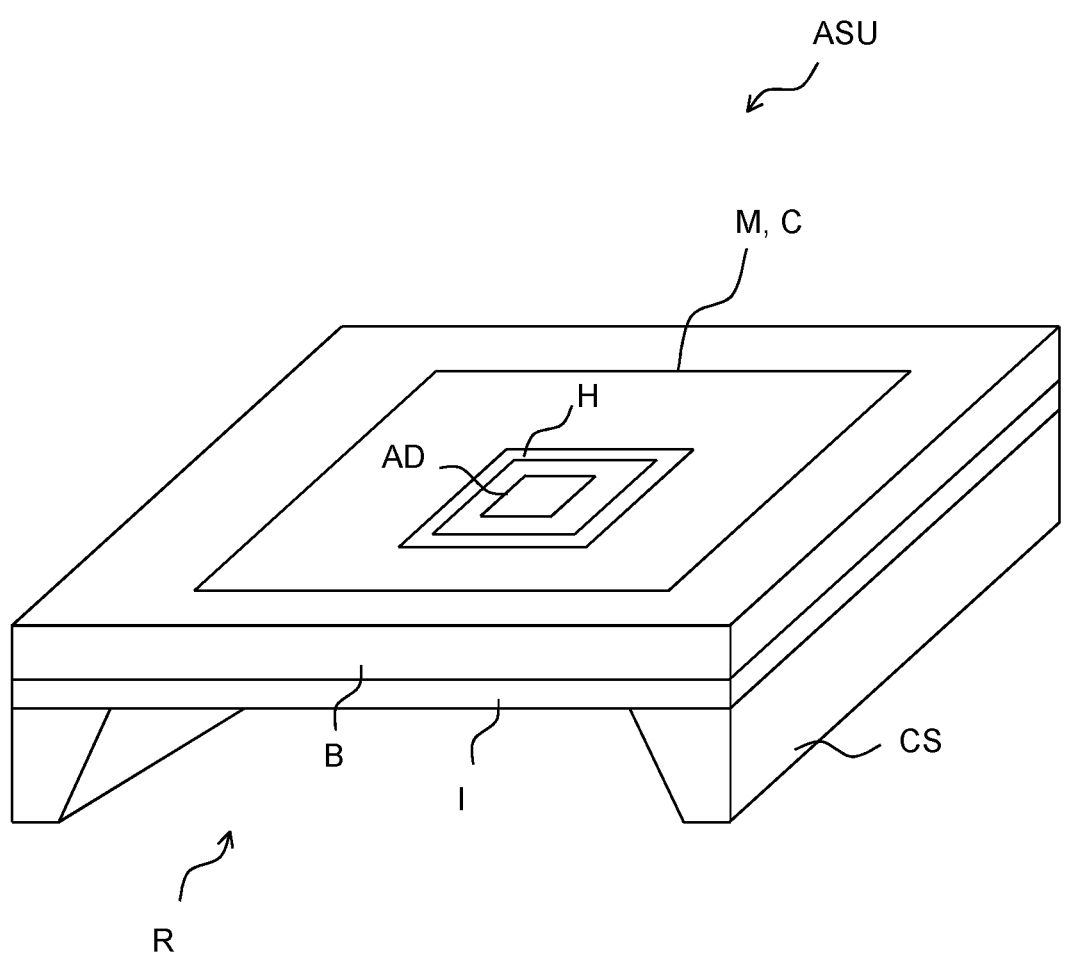
FIG. 2 shows the special arrangement of corresponding elements of a gas sensor component in a perspective view.

FIG. 2 illustrates a possible physical arrangement of the heater H and of the active detector AD of the active sensor unit ASU of the gas sensor. The heater H and the active detector AD can be arranged on a membrane M. The heater H and/or the active detector AD of the active sensor unit ASU can be covered with the material of the catalyst C. A carrier substrate CS can be provided to carry an insulator I, on which the base B carrying the membrane M is arranged. A recess R provided at the bottom side of the carrier substrate CS together with recesses or holes of the insulator I and of the base B allow the mass of the thermally active elements to be small as possible, reducing thermal inertia and reducing the response time necessary for a change in the concentration of the to-be-monitored gas.

However, it is possible that the carrier substrate CS, the insulator I and the base B also carry the reference sensor unit with the reference detector and the heater of the reference sensor unit such that a small and compact gas sensor component can be obtained. However, it is preferred that the catalyst only covers one of the two sensor units while the other sensor unit is free from the catalyst.

The gas sensor and the gas sensor component are not limited to the specific details described above and shown in the Figures. The gas sensor can comprise further circuit elements, e.g. for stabilizing the temperature control. The gas sensor component can comprise further elements such as a housing, external contacts, power connections, signal connections and the like.

The invention claimed is:

1. A gas sensor with improved sensitivity, comprising
    an active sensor unit with an active detector, an active-sensor heater, and a catalyst,
    a reference sensor unit with a reference detector and a reference-sensor heater,
    a temperature control circuit provided and configured to keep the active detector at a constant, predetermined temperature,
    wherein the temperature control circuit comprises an operational amplifier with an inverted input, a non-inverted input, and an output, and wherein the output of the operational amplifier is electrically coupled directly to the active-sensor heater of the active sensor unit and directly to the reference-sensor heater of the reference sensor unit.

2. The gas sensor of claim 1, wherein the catalyst determines the gas selectivity.

3. The gas sensor of claim 1, wherein the active detector and the reference detector are electrically connected in series.

4. The gas sensor of claim 1, wherein the active-sensor heater of the active sensor and the reference-sensor heater of the reference sensor are electrically connected in parallel.

5. The gas sensor of claim 1, wherein the temperature control circuit provides electrical power to the reference-sensor and the active-sensor heaters.

6. The gas sensor of claim 1, wherein
    the active detector is thermally coupled to the active-sensor heater of the active sensor unit and
    the reference detector is thermally coupled to the reference-sensor heater of the reference sensor unit.

7. The gas sensor of claim 1, wherein
    the inverted input is coupled to a supply voltage and
    the non-inverted input is coupled to a first node at the output side of the active-sensor heater of the active sensor unit.

8. The gas sensor of claim 1, comprising a signal port having a connection coupled to a second node between the active detector and the reference detector.

9. The gas sensor of claim 8, comprising an evaluation circuit connected to the signal port.

10. The gas sensor of claim 9, wherein the evaluation circuit comprises an application-specific integrated circuit, a microcontroller and/or an analog-to-digital converter.

11. A gas sensor component, comprising the gas sensor of claim 1, wherein the active sensor unit is arranged at a membrane at the top side of a base material, the base material being arranged on or above a carrier substrate comprising a recess.

* * * * *